United States Patent
Young et al.

(10) Patent No.: US 6,425,906 B1
(45) Date of Patent: Jul. 30, 2002

(54) ULTRASONIC CUTTING TOOL

(76) Inventors: Michael John Radley Young; Stephen Michael Radley Young, both of Ashburton (GB)

(*) Notice: Subject to any disclaimer, the term of this patent is extended or adjusted under 35 U.S.C. 154(b) by 0 days.

(21) Appl. No.: 09/530,966
(22) PCT Filed: Jan. 19, 1999
(86) PCT No.: PCT/GB99/00162
§ 371 (c)(1), (2), (4) Date: Jun. 28, 2000
(87) PCT Pub. No.: WO99/35982
PCT Pub. Date: Jul. 22, 1999

(30) Foreign Application Priority Data

| | | |
|---|---|---|
| Jan. 19, 1998 | (GB) | 9801088 |
| Feb. 25, 1998 | (GB) | 9803896 |
| Jun. 11, 1998 | (GB) | 9812556 |
| Oct. 23, 1998 | (GB) | 9823194 |
| Jan. 6, 1999 | (GB) | 9900170 |

(51) Int. Cl.$^7$ ............................................. A61B 17/32
(52) U.S. Cl. ........................................ 606/169; 606/171
(58) Field of Search ............................... 606/1, 37, 39, 606/40, 45, 46, 52, 169–171; 604/22

(56) References Cited

U.S. PATENT DOCUMENTS

| | | | | |
|---|---|---|---|---|
| 5,322,055 A | * | 6/1994 | Davison et al. | 606/169 |
| 6,004,335 A | * | 12/1999 | Vaitekunas et al. | 606/1 |
| 6,056,735 A | * | 5/2000 | Okada et al. | 606/169 |
| 6,129,735 A | * | 10/2000 | Okada et al. | 606/169 |

* cited by examiner

*Primary Examiner*—Jeffery R. Jastrzab
(74) *Attorney, Agent, or Firm*—Oblon, Spivak, McClelland, Maier & Neustadt, P.C.

(57) ABSTRACT

A surgical tool for cutting and/or coagulating tissue includes a piezo-electric driver to generate ultrasonic energy including torsional mode vibrations. A waveguide is operatively connected at a proximal end to the driver and extends a distance of $n\lambda_{T/2}$, where $\lambda_T$ is the wavelength of ultrasonic vibration in the material of the work horn or waveguide. A distal end of the waveguide is provided with a cutting and/or coagulating tool.

15 Claims, 16 Drawing Sheets

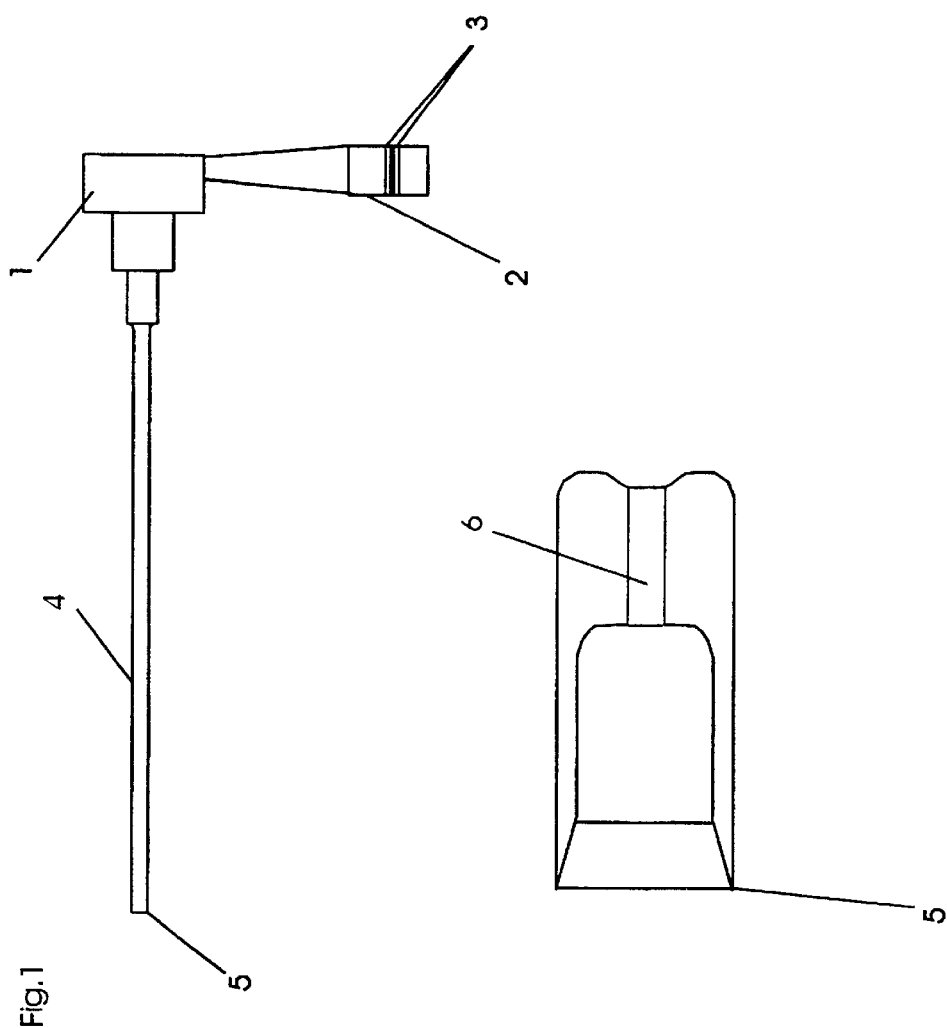
Fig.1
Fig 1A
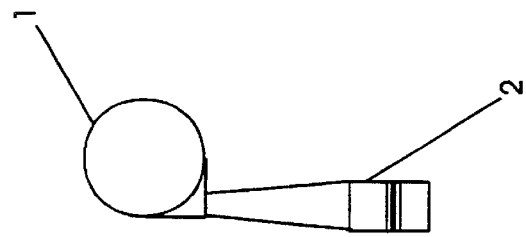
Fig1B

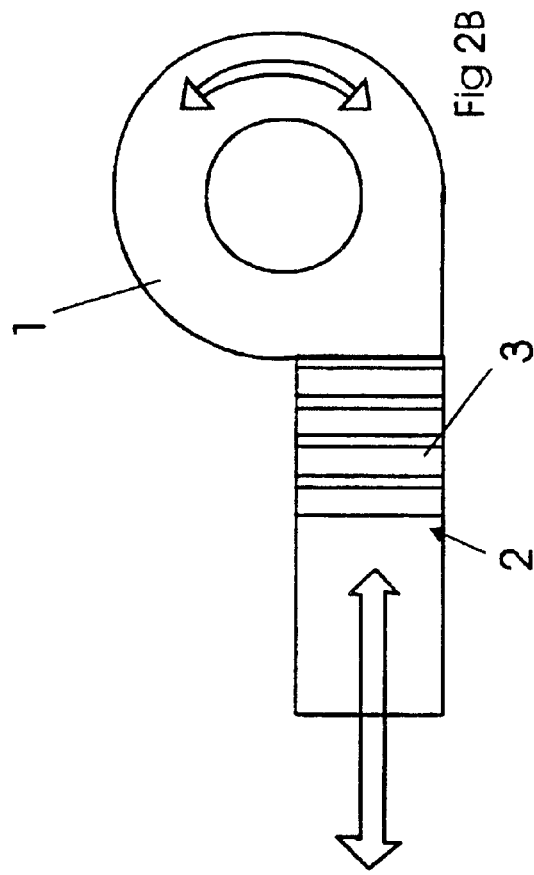
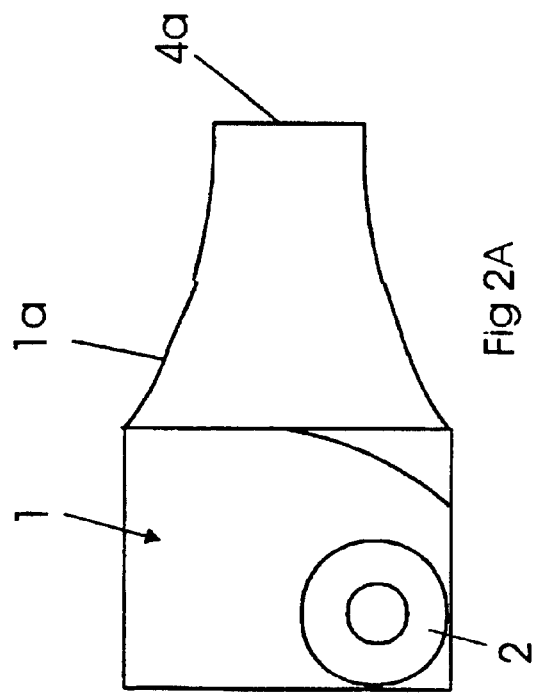

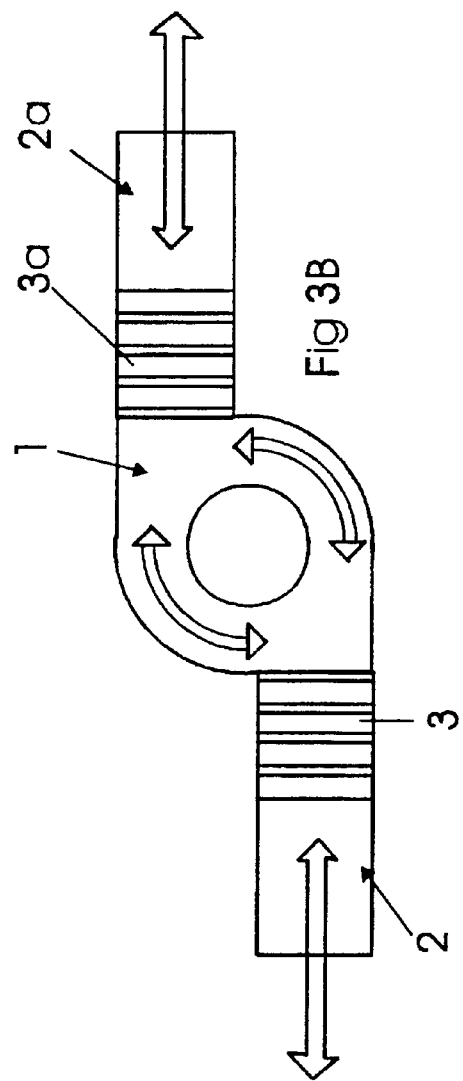
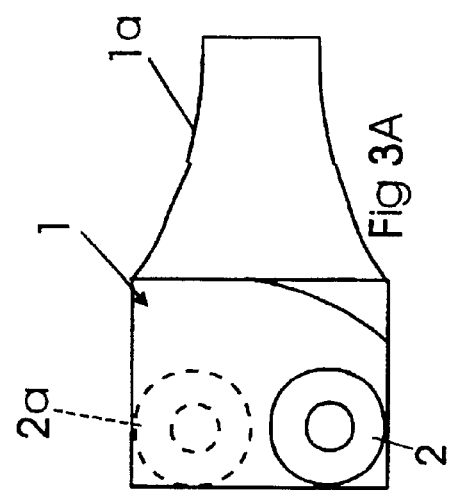

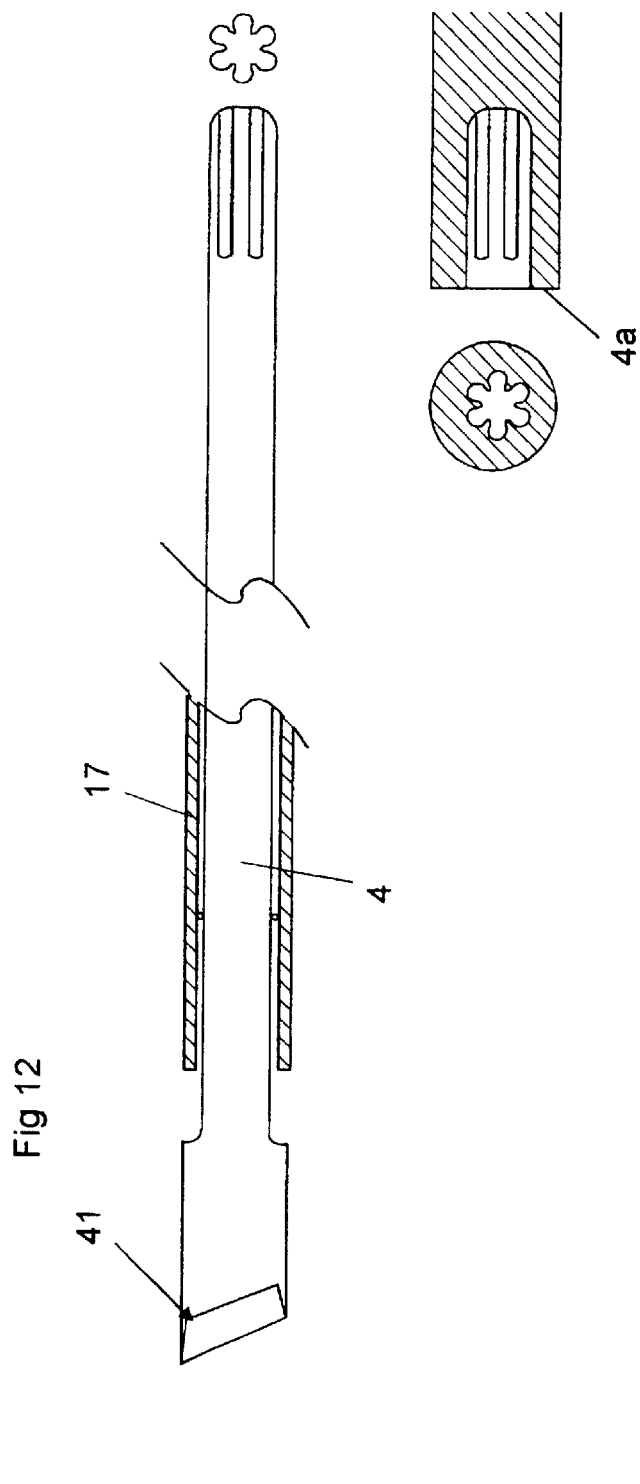

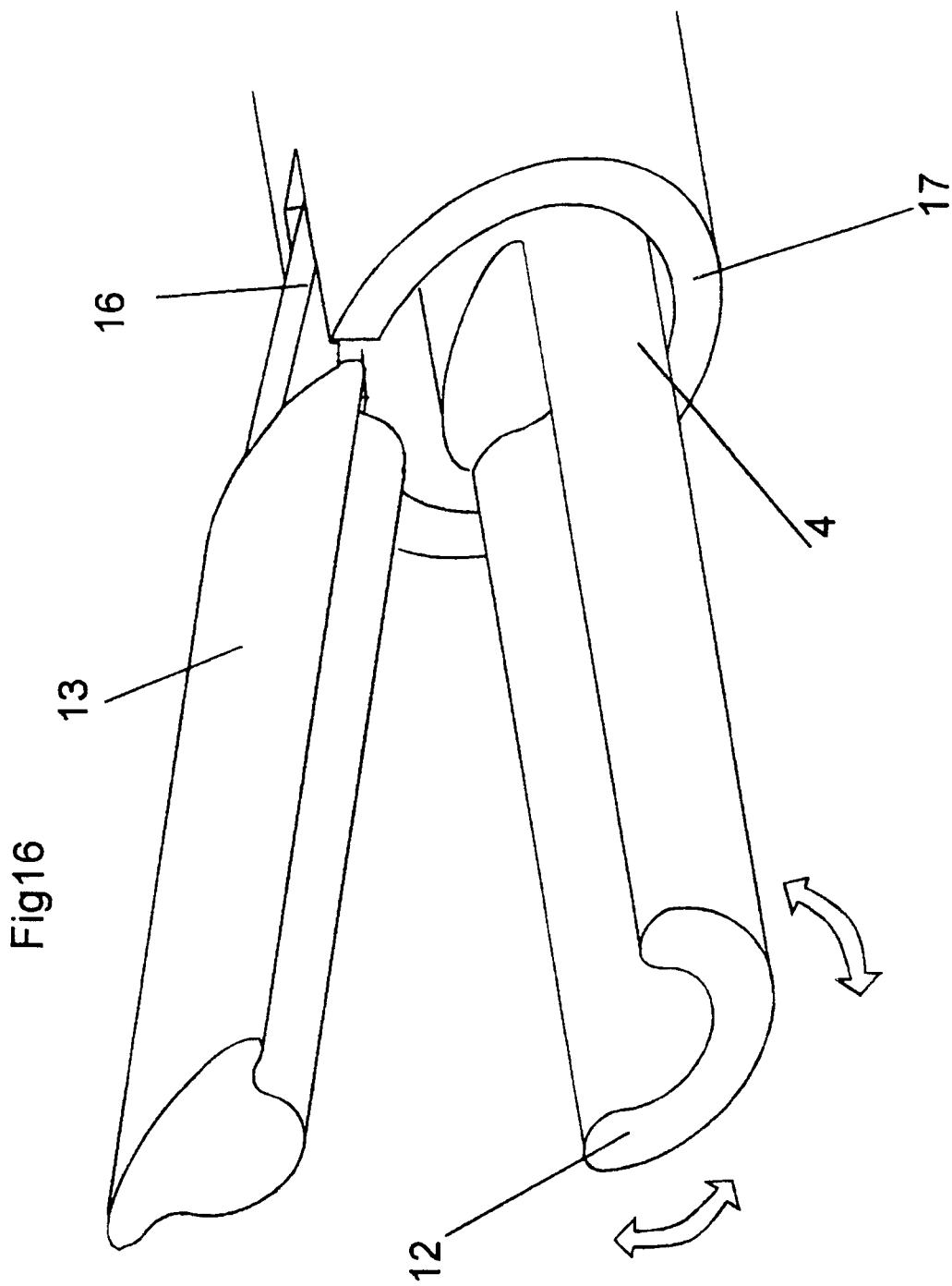

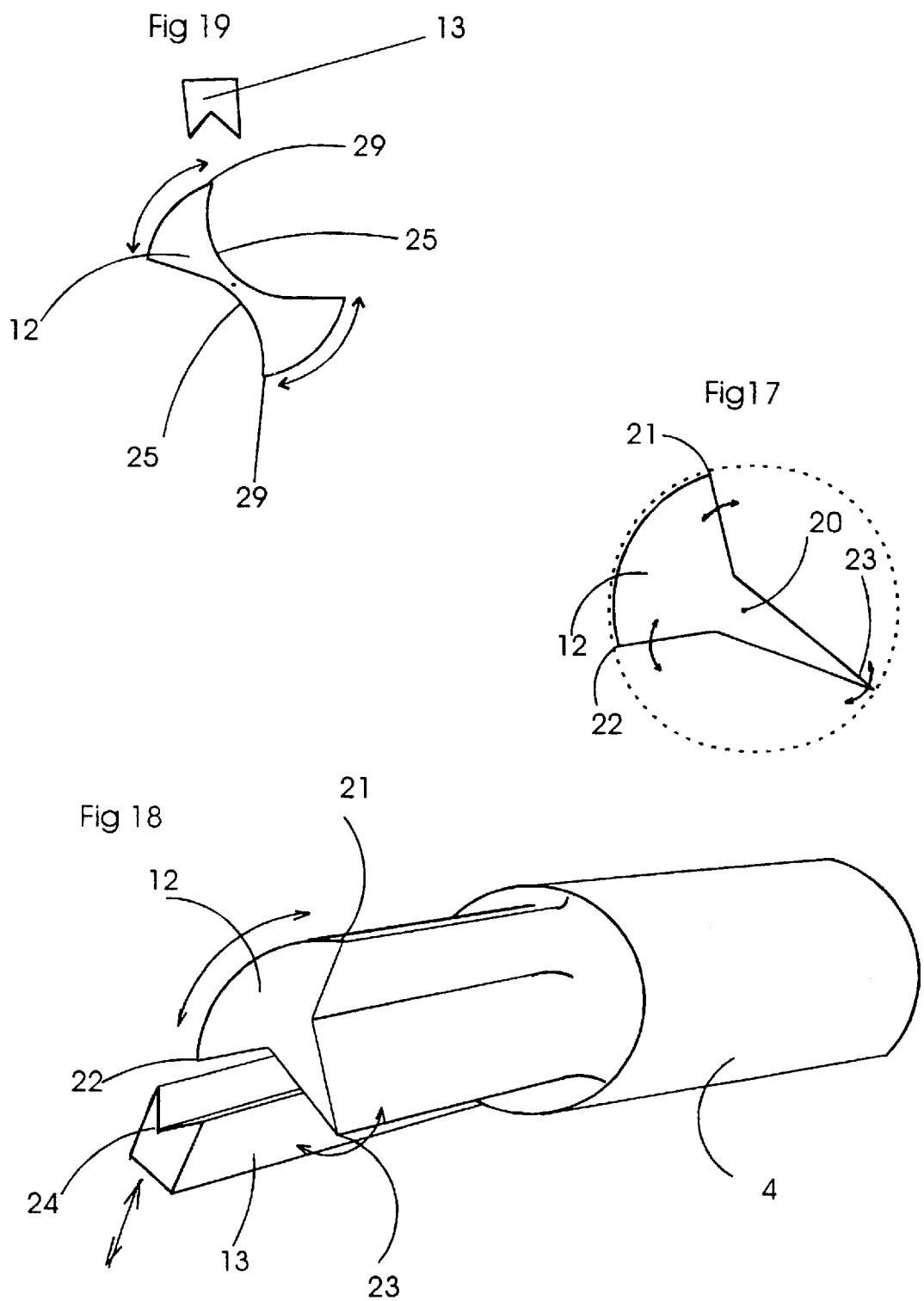

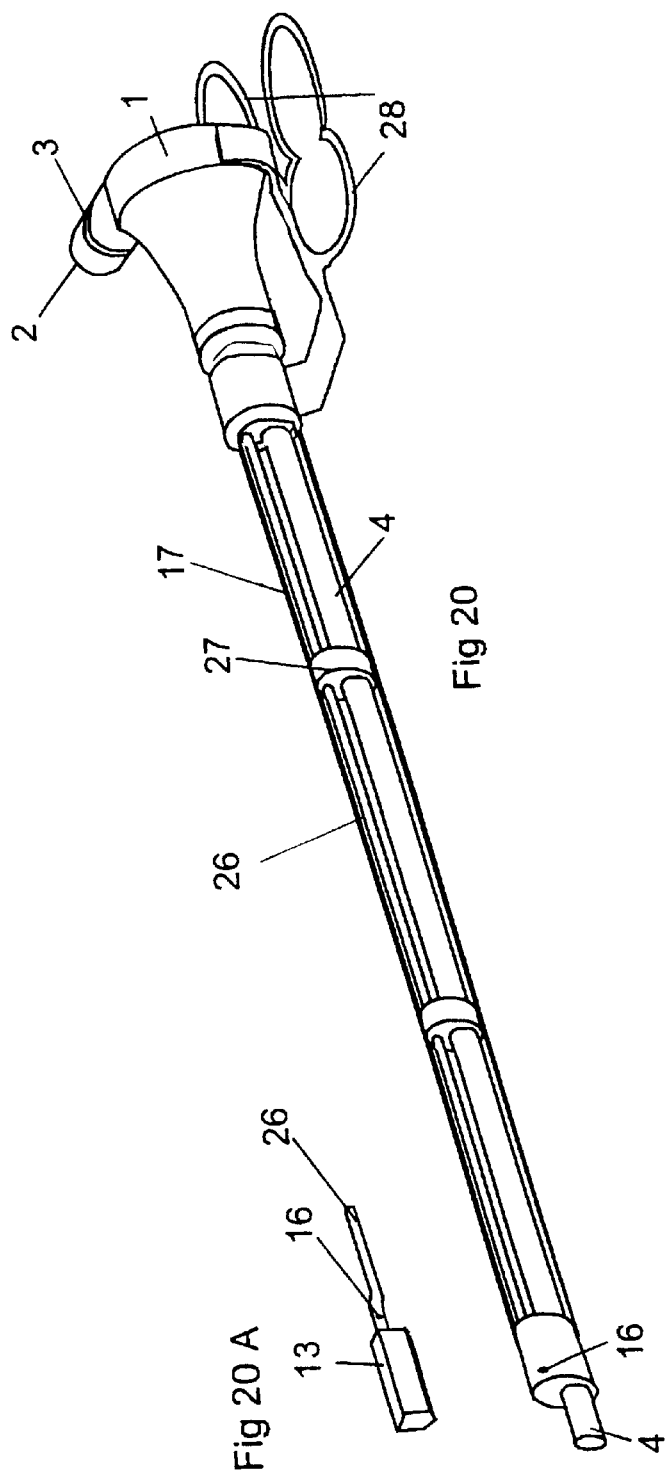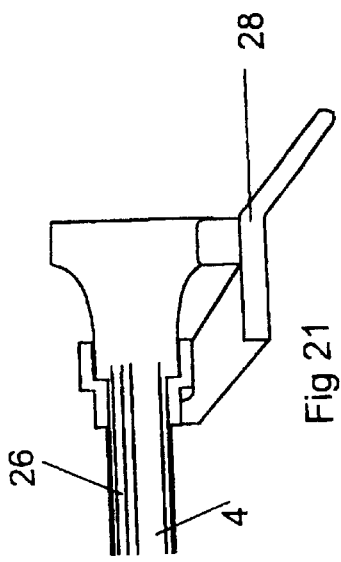

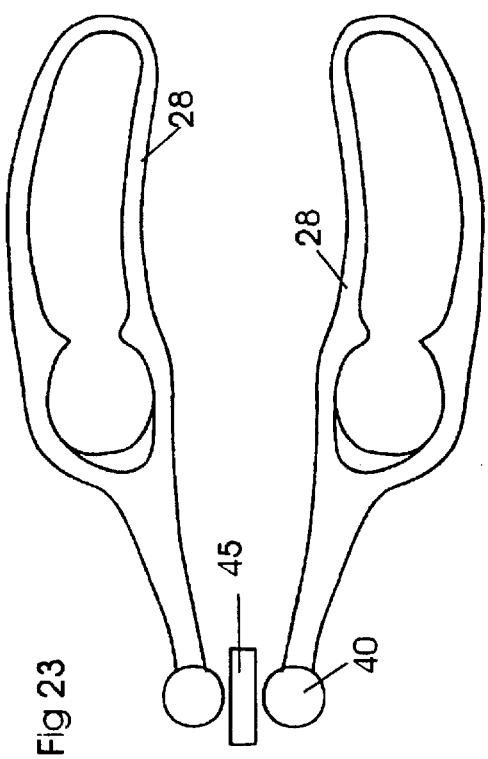
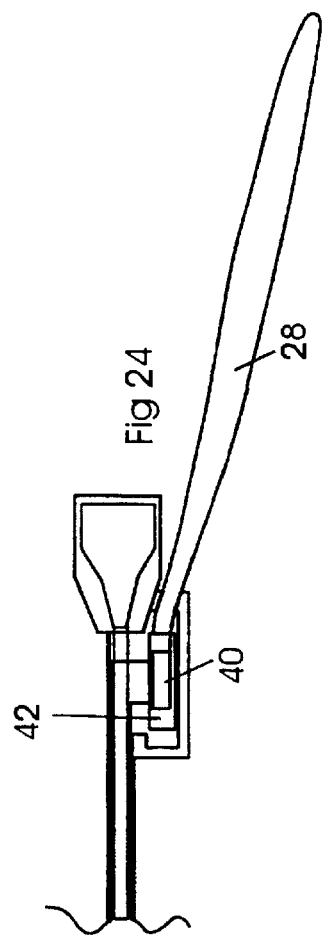
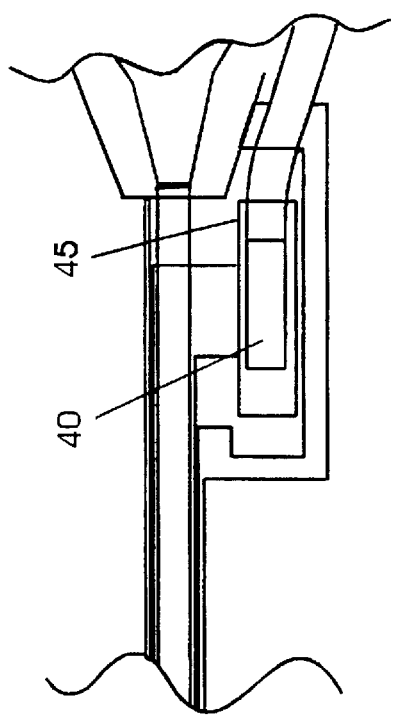

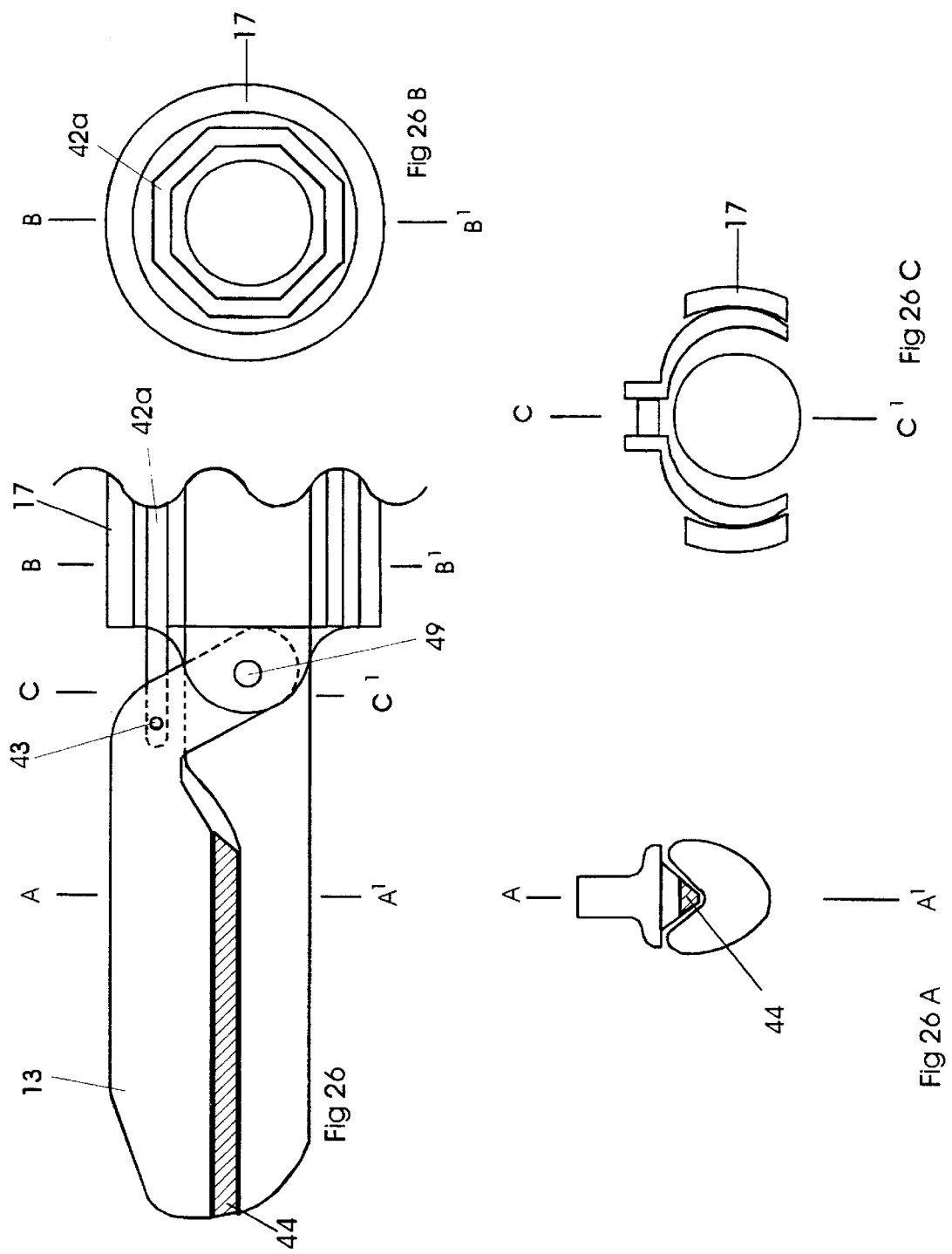

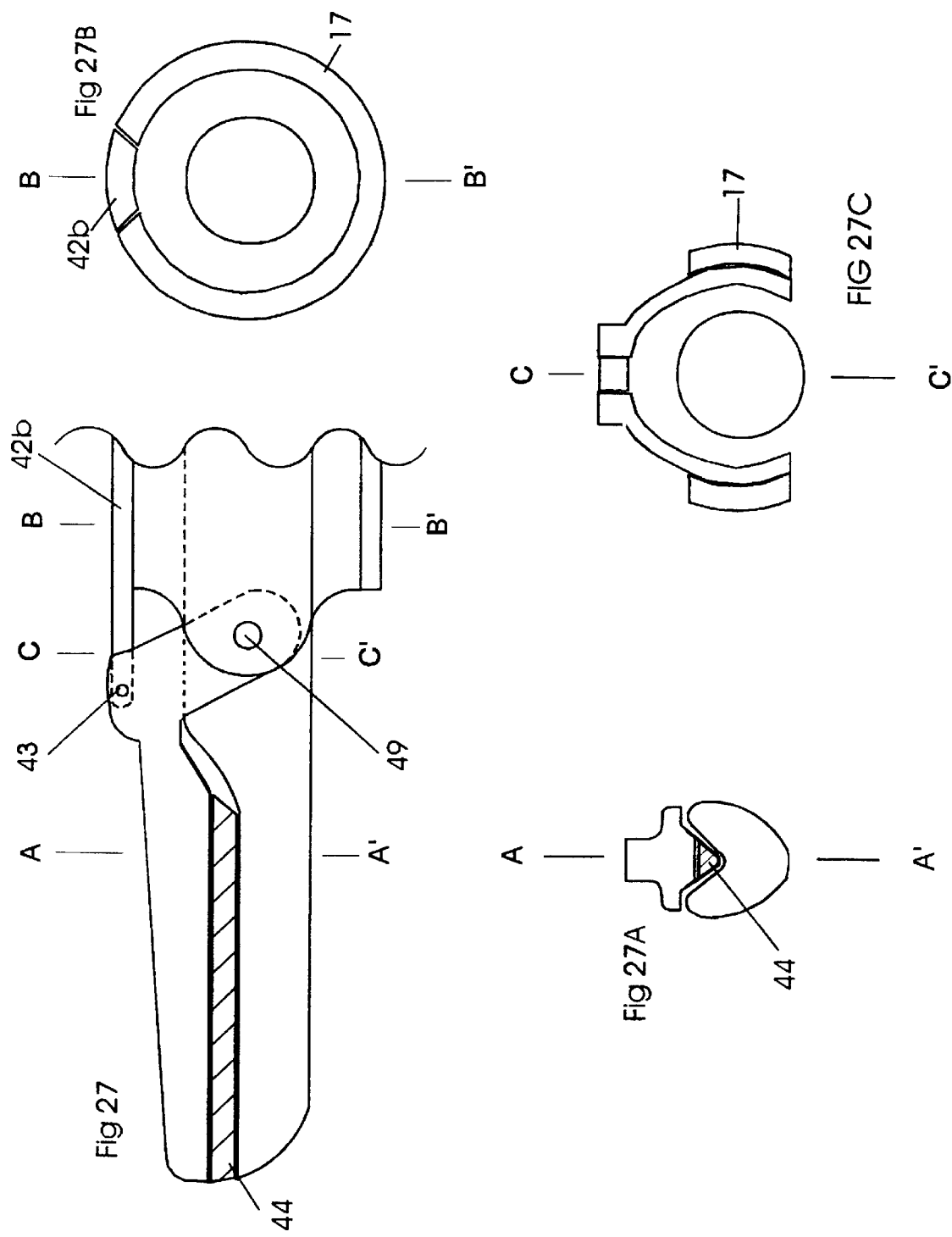

ULTRASONIC CUTTING TOOL

TITLE OF THE INVENTION

BACKGROUND OF THE INVENTION

1. Field of the Invention

The present invention relates to an ultrasonic cutting tool. More particularly, but not exclusively, it relates to a tool for cutting material, especially soft material such as flesh. It may be useful in a laparoscopic cutting system particularly for haemostatic cutting.

2. Discussion of the Background

It is known to cut tissue by means of ultrasonically vibrated knives or scalpels. When a scalpel cuts tissue its effectiveness is indicated by the cutting force. This derives from the pressure required to separate the structure and from the frictional drag as the blade is drawn between the cut sections. Vibrating the blade can reduce friction and may also reduce the bond strength of the tissue. Both objectives could be achieved by applying vibrations to the cutting blade in either a longitudinal or torsional mode.

However, only axial mode oscillatory systems have been used hitherto. These can produce appropriate conditions for soft tissue cutting, controlled coagulation and aspirated dissection. Longitudinal compression waves couple most efficiently to achieve effective transmission but we believe it is incorrect to assume that this mode is optimally deployed for a wide range of surgical applications. Caution must be exercised when applying ultrasound at intensities in the order of hundreds of watts per $cm^2$.

It is now well known that longitudinal mode vibrations can safely be applied in specific orthopaedic procedures involving bone cement removal. In such cases it is appropriate to use longitudinal vibration modes since the acoustic properties of the prosthetic cement and bone tissue ensure minimal transmission from the operating site. However, this situation is unusual and generally it is necessary to take special precautions when using high intensity ultrasound to effect tissue removal in potentially vulnerable regions of the anatomy.

At frequencies in the low kHz range, pressure and displacement waves transmit deep into human tissue since absorption rates at these relatively low frequencies are quite low. However, due to the unpredictable transmission path, standing waves can occur leading to local increased absorption and heating. At energy levels applied in tissue cutting there is a significant risk of creating cell damage in areas remote from the operating site. Ultrasound energy is absorbed in three ways, by frictional heating due to relative cyclic motion at the instrument tissue interface by direct absorption in the molecular structure of the excited tissue and by cavitation. Frictional transmission produces local heating adjacent to the activated instrument surface and is inherently safe. However, cavitation and direct molecular absorption can lead to damaging effects which in extreme cases could be harmful.

Mechanical power transmission is defined by the product of oscillatory force and oscillatory velocity amplitudes, and in the case of a longitudinal mode system loaded in a direction normal to the axis of vibration, i.e. displacement parallel to a transmission interface, this is given by:

$$i\ P_L = 1/2 F_f d\xi_L/dt \tag{1}$$

where $P_L$ is the r.m.s. power, $F_f$ is the frictional force amplitude and $\xi_L$ is the particle displacement amplitude normal to the clamping force between blade and tissue. The frictional force acts in a direction parallel to the longitudinal vibration but is a function of the clamping force and a term defining the frictional drag between the blade and tissue at the transmission interface. This term may vary in time (correlated with the longitudinal vibration) between values of 0 and 1 representing zero or full coupling between blade and tissue.

For torsional mode, i.e. displacement normal to a transmission interface, power transmission is given by:

$$P_T = 1/2 F_T d\xi_T/dt \tag{2}$$

Where $P_T$ is the r.m.s. power, $F_T$ the oscillatory force amplitude and $\xi_T$ the torsional displacement amplitude.

In the case of a polished blade being pressed normally onto tissue it is reasonable to assume that the normal clamping force is small compared with the direct force amplitude $F_T$. If the friction force $F_f = 0.1\ F_T$ for instance, then from equations (1) and (2):

$$P_T = 10 P_L,$$

assuming similar tissue loading conditions (blade tissue impedance), and $d\xi_L/dt = d\xi_T/dt$.

It is therefore evident that the energy transmission may be an order of magnitude higher in the case of an appropriately designed torsional cutting head relative to a corresponding longitudinal mode system.

Qualitative transmission characteristics can be simply demonstrated by immersing the head in water. If a longitudinal mode system is immersed in water but with the distal end just above the surface and in air, minimal water disturbance is noted. By contrast, a grooved torsional mode system, providing two exposed normal mode surfaces, shows focused transmission perpendicularly out of the groove. In the absence of such surfaces, so that only shear mode frictional coupling equivalent to the longitudinal system is present, virtually no transmission is observed.

In contrast, transmission from the immersed distal end face of a longitudinal system demonstrates the anticipated high intensity cavitation field with considerable collateral damage potential.

The importance of normal mode interaction between the energised system and the tissue is described by Balamuth U.S. Pat. Nos. 3,636,943 and 3,862,630, in which is described a longitudinal mode vibration being used in conjunction with a clamp, acting parallel to the direction of energy propagation, to grasp tissue and press it onto the vibrating work piece, enabling coupling between the two. The apparatus described in the patents did this at the end face of the work piece.

Ultracision U.S. Pat. No. 5,322,055, follows the clamping principle but the system described actuates the clamp perpendicular to the direction of energy propagation. As described above shear mode interaction only is utilised and this requires high clamping pressure. The present invention applies clamping parallel to the direction of energy propagation but does so via a groove along the distal side of the work piece.

SUMMARY OF THE INVENTION

It is one object of the present invention to provide an oscillatory system so that the activated cutting head vibrates in a torsional mode with minimal compression wave transmission beyond the distal extremity.

Although less easily achieved within the necessary constraints associated with surgical applications, there are clear advantages to be gained from the use of torsional mode radiation. Use of torsional mode vibrations is more efficient since maximum coupling can be achieved by transmission into tissue in a direction normal to the axis of the instrument. In the case of longitudinal mode vibrations, normal mode transmission occurs along the length of the instrument only by virtue of frictional effects (see above).

Use of torsional mode vibrations is also safer since energy is absorbed in the target tissue and not transmitted along a probe axis into distant regions.

Also, a torsional mode transducer is more easily accommodated within a scissors handgrip (such as is preferred by surgeons). It therefore gives ergonomic design advantages, and it is a further object of the invention to provide a cutting device having scissors type action.

Higher cutting efficiency will require less electrical power input allowing smaller energy converters and no need for cooling systems.

According to the present invention, there is provided a surgical tool comprising means to generate ultrasonic torsional mode vibrations, a waveguide operatively connected at a proximal end to said generating means and extending a distance therefrom of $n\lambda_T/2$ (where $\lambda_T$ is the wavelength of ultrasonic vibration in the material of the waveguide) to a distal end provided with cutting and/or coagulating means.

The cutting means may comprise a torsionally vibratable element connected to said waveguide in combination with a static element.

Preferably, the means to generate ultrasonic torsional mode vibrations comprises a conversion horn and at least one axial mode driver mounted substantially tangentially thereto.

Advantageously, a shroud is provided to surround and isolate the waveguide along at least a portion of its length.

In this case said static element of the cutting means may be mounted to said shroud, whereby it is isolated from said torsional vibrations.

Preferably, said cutting means has a cutting face between said static and vibrational elements which is normal to the general direction of said torsional vibrations.

A pair of cutting faces normal to the direction of said torsional vibrations may be provided, said pair of faces intersecting at or adjacent an axis of said waveguide.

The cutting means may comprise a plurality of cutting faces, at least one of which is substantially normal to the general direction of said torsional vibrations.

Alternatively or additionally the cutting means may comprise a plurality of cutting faces, at least one of which is substantially parallel to the general direction of said torsional vibrations.

Alternatively or additionally, at least one cutting face may be angled with respect to the general direction of said torsional vibrations, whereby it is acted upon by both normal and parallel components thereof.

In either of the first or second aspects said cutting means may be aspirated by means of a passage extending along or parallel to the waveguide to a vacuum source.

BRIEF DESCRIPTION OF THE DRAWING

Embodiments of the present invention will now be more particularly described by way of example and with reference to the accompanying drawings, in which:

FIG. 1 shows schematically an ultrasonic cutting tool driven by torsional mode vibrations;

FIG. 1A is a scrap view of a distal end of the apparatus of FIG. 1;

FIG. 1B is an end elevation of the apparatus of FIG. 1;

FIGS. 2A and 2B show respectively a side view and an end elevation of an alternative torsional mode generator, FIGS. 3A and 3B show respectively a side view and an end elevation of a further alternative torsional mode generator having twin drivers;

FIGS. 10 and 10A show in perspective and cross sectional view a distal end embodying a combination of those shown in FIGS. 8 and 9;

FIG. 12 shows a distal end of the waveguide of greater diameter than the waveguide itself and a shroud surrounding the waveguide up to the distal end;

FIG. 13 shows various torsional coupling schemes for connecting the basal end of a waveguide to a torsionally vibratable head;

FIG. 16 shows a perspective view of a distal end of a coagulation tool of the type indicated in FIG. 15;

FIG. 17 shows schematically and in cross section a distal end adapted for cutting;

FIG. 18 is a perspective view of a distal end of a cutting tool as indicated in FIG. 17;

FIG. 19 shows in cross section a combination distal end adapted for cutting and coagulating;

FIG. 20 shows a perspective view of another embodiment of ultrasonic cutting tool;

FIG. 20A indicates schematically a distal end of the tool;

FIG. 21 shows in longitudinal cross section, a proximal end of the tool of FIG. 20, including a transducer and gripping handles;

FIG. 23 is a plan view of the operating mechanism including gripper handles;

FIG. 24 shows the operating mechanism of FIGS. 22 and 23 in longitudinal cross section;

FIG. 25 is a view to an enlarged scale of the central portion of FIG. 24;

FIG. 26 is a cross sectional view of the distal end of a cutting tool, of which the proximal end incorporates an operating mechanism as shown in FIGS. 22 to 25;

FIGS. 26A, 26B and 26C are transverse cross sectional views taken respectively along the lines A–A', B–B', and C–C' of FIG. 26;

FIG. 27 is a cross sectional view of a distal end of an alternative further embodiment of cutting tool to that shown in FIG. 26; and FIGS. 27A, 27B and 27C are cross sectional views taken along the lines A–A', B–B' and C–C' of FIG. 27.

DESCRIPTION OF THE PREFERRED EMBODIMENTS

Figure 4A:
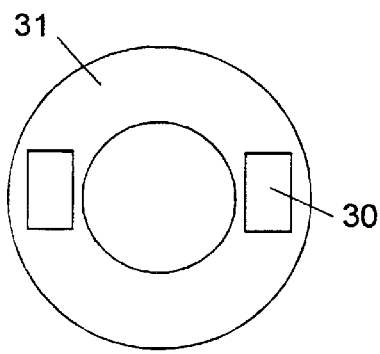
FIGS. 4A and 4B show respectively plan and side views of an alternative source of ultra sound vibration including two shear mode transducers acting on a concentrator to give torsional vibrations.

Referring now to the drawings, there is shown in FIG. 1 an ultrasonic cutting tool in which an axial mode driver 2 is mounted tangentially to a stepped horn 1 to cause torsional mode vibration thereof. The driver 2 is powered by means of piezo-electric ceramic transducers 3.

An elongate waveguide 4 is operatively connected at a proximal end to the stepped horn 1 and at its distal end has a cutting edge 5, or may have any other suitable device, as described below. The length of the waveguide 4 is $n\lambda_T/2$ (wherein $\lambda_T$ is as defined above). As shown, the cutting edge 5 forms an annulus surrounding a cavity connected to a vacuum suction source (not shown) by means of a passage 6 extending the length of the waveguide 4.

FIGS. 2A and 2B show an alternative system for converting longitudinal vibration of an axial drive transducer 2 into a torsional vibration in a conversion horn 1. The axis of the axial transducer 2 is displaced from the axis of the conversion horn, but the axis of the conversion horn 1 is normal to the axis of the driver 2. The arrangement induces a torque on the horn about its own axis.

The vibration imparted to the horn 1 by the driver 2, will circulate the horn 1. The combination resonates (in the fundamental) when the mean circumference of the horn 1 is equal to the wavelength of the axial mode generated by the transducer 2.

Amplitide amplification is provided by a (lower gain) exponential curve 1a towards the horn output end 4a, to which a waveguides 4 may be connected.

FIGS. 3A and 3B show an alternative system for converting longitudinal vibration of two axial drive transducers 2 and 2a into a torsional vibration in a conversion horn 1. The axes of the axial transducers 2 and 2a are displaced symmetrically about the axis of the conversion horn but parallel to each other. The axis of the conversion horn is normal to the axes of the drives 2 and 2a which are directed oppositely. The arrangement induces a torque on the horn about its own axis in the same manner as described above but with the advantage that each axial transducer 2 and 2a can be driven with less power than the single one of FIGS. 2A and 2B.

To compensate for the phase shift between the motions of the two axial transducers around the horn ie equivalent to $\lambda/2$, the voltage supplied to the axial drivers 2 and 2a is derived from a dual supply generator controlling a phase shift between the two voltages.

Figure 4B:
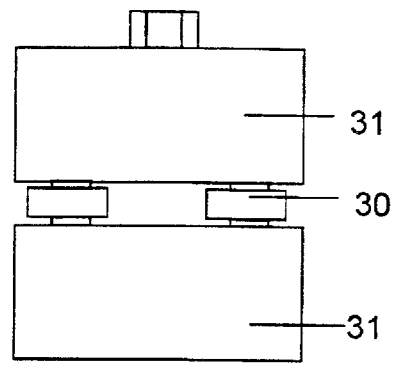

Referring now to FIGS. 4A and 4B, there is shown a torsional mode transducer in which two opposed pairs of shear mode vibratable piezo-electric ceramic crystals 30 are mounted between two halves of an annular body 31 to be able to cause relative displacement of the two halves of annular body 31 in a plane perpendicular to the sheet as shown in FIG. 4B, causing torsional vibrations in the body. The direction of polarisation of each crystal should lie in the same direction, which is normal to the displacement direction. The shear mode crystals 30, of which there may be two or more, are arranged in a radial manner around a circumference of predetermined pitch diameter.

Figure 5A:
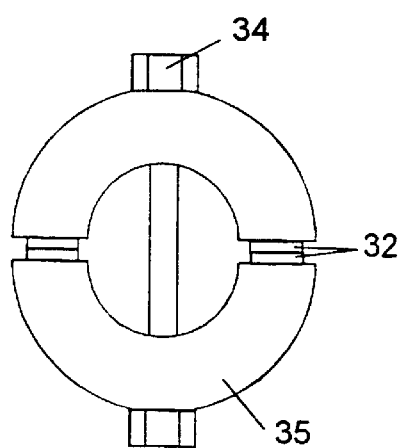
FIGS. 5A and 5B show respectively plan and side views of a further source of ultrasonic vibrations including two axially vibratable piezo ceramic transducers arranged to give torsional vibrations in a cylindrical body.
Figure 5B:
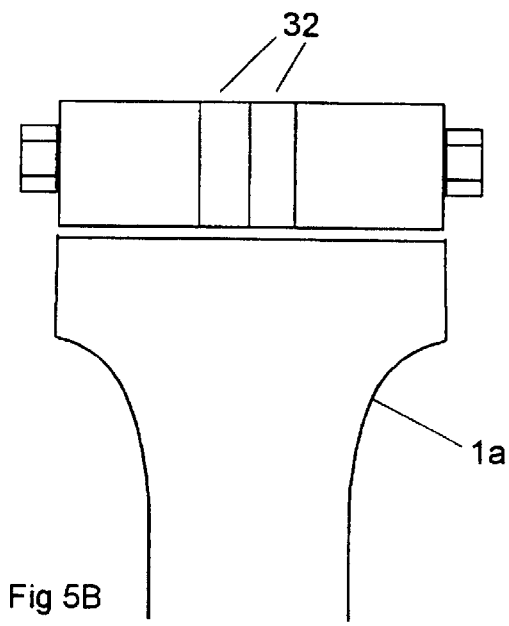

Referring now to FIGS. 5A and 5B, a further form of torsional mode transducer is shown, in which two opposed pairs of axially vibratable piezo ceramics 32 are mounted between two half cylindrical shell pieces 33. The shell pieces 33 are held together by a retaining bolt 34 to form a cylindrical transducer. Each pair of piezo ceramics is driven exactly out of phase to the others, thus creating a displacement which is tangential to the cylindrical shell, with the combination of effects giving rise to a torsional mode vibration.

In either of the trnsducer embodiments shown in FIGS. 4 and 5, the transducer arrangement may be bonded to the waveguide or may be integral therewith. Such transducers may be used in conjunction with any of the embodiments of cutting tool described herein. FIGS. 6 to 11 show various embodiments of distal end cutting (and cauterising) systems.

In general the cutting or cauterising (distal) end comprises a pair of blades which together are generally conical to facilitate insertion into and between tissue strands.

A static (i.e. non-vibrating) blade 13 of the pair is hinged by hinge 16 or otherwise connected to a distal end of the isolation sleeve 17 over the waveguide 4 to form a static element of a pair of scissors type blades. Means may be provided to open the scissors, whereby the user can separate tissue just as with current laparoscopic instruments, and can move to clamp around tissue or blood vessels.

Torsional mode vibration provides concentric motion about the axis of the waveguide 4 and the vibrating blade 12. Sections of the blade non-parallel with the motion provide vibrating faces 14 capable of imparting energy directly into tissue brought to bear on such a face rather than cause friction as in conventional, parallel motion devices. The face may be normal to the motion or at an intermediate angle thereto, i.e. any angle between 1°–179°, although 60°–120° is preferred, and 90° may be most advantageous.

Tissue is trapped between the closing blades and the speed and ease of cutting and blood coagulation will depend on the mode and amplitude of the vibration and the geometry of the blades, designed to utilise the torsional mode of the vibrating blade.

In general, the blades are shaped so that one has a sector shaped cross section and the other has a cross section of a circle more or less missing the corresponding sector, so that the two blades meet at a vee.

When the blades are to be used for cutting, it is preferred that the "male" blade is a sector of included angle less than the angle between faces of the "female" blade. When the blades are to be used for cauterising, it is preferred that the included angle of the "male" blade is greater than the angle between faces of the "female" blade.

Figure 6:
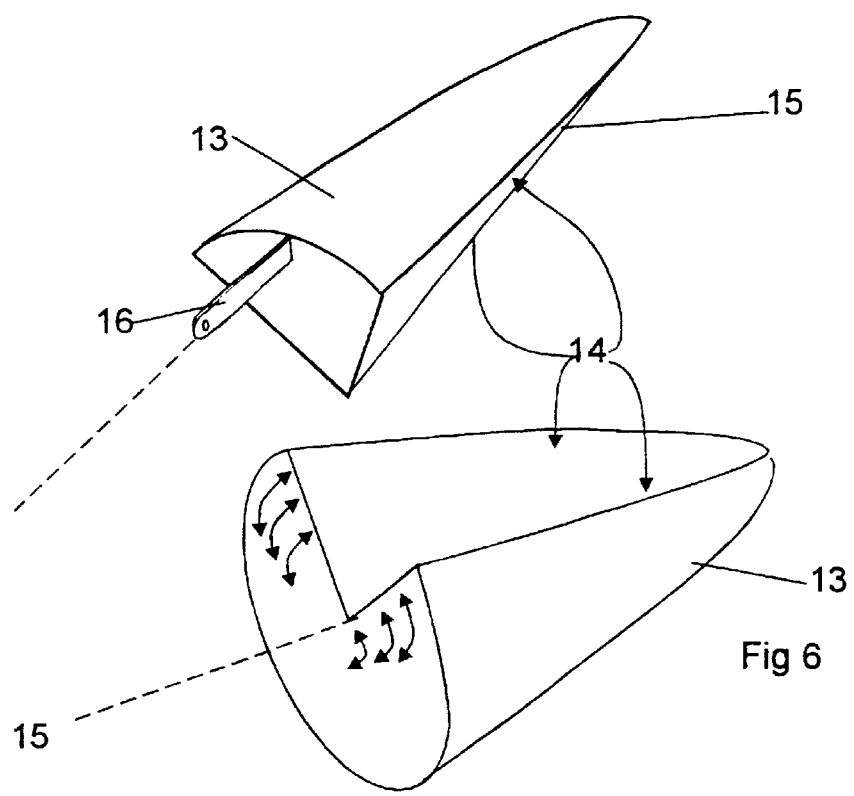
FIG. 6 shows a distal end of a tool having two surfaces normal to the motion coacting with a matching static blade movable into and out of engagement with the vibrating blade.

In FIG. 6 the cutting end comprises a vibratable blade 12 and a static blade 13. The vibratable blade 12 has two radial cuts into the vibrating blade 12 spaced angularly at 1°–120°, or as shown c.90°, to provide two surfaces 14 normal to the motion. (Even surfaces spaced at an angle up to 179° could be envisaged) The matching static blade 13 traps tissue against both faces. The faces meet along a straight edge 15 which is parallel to the axis of the waveguide 4. The static blade 13 is provided with an extension 16 by which it may be attached pivotally to the shroud 17.

Figure 7:
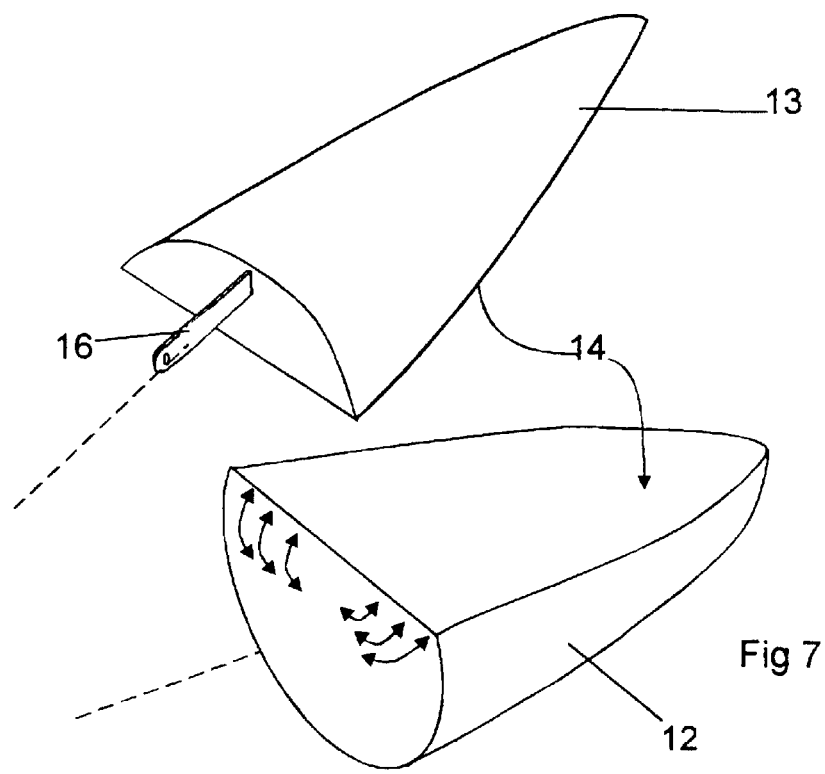
FIG. 7 shows a distal end having a surface normal to the motion for lower intensity cutting/coagulation over a large area.
Figure 8:
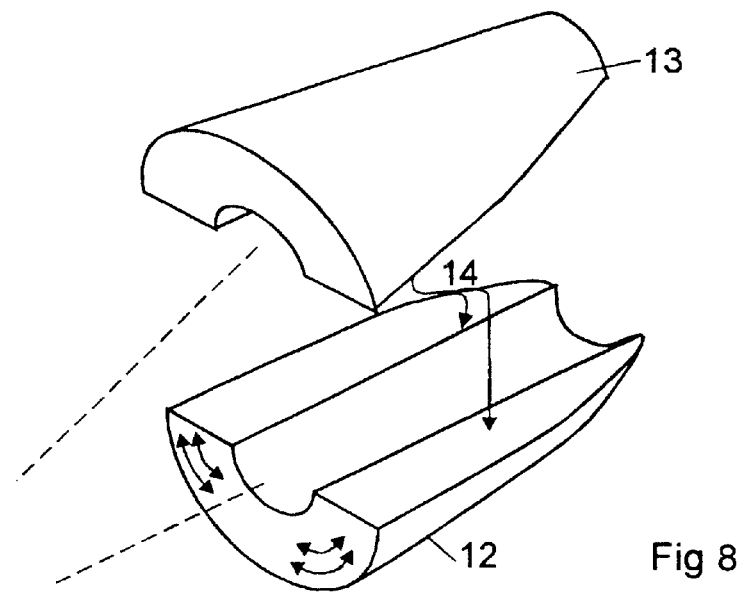
FIG. 8 shows a distal end adapted from that shown in FIG. 7 adapted for contact around an axis zone in which motion is zero or small.

FIG. 7 shows a cutting end with a single planar section through the axis separating the cutting end into vibratable 12 and static 13 blades coacting over one large surface 14 normal to the motion for lower intensity cutting/coagulation over a large area FIG. 8 shows a cutting end which is an adaption of the above FIG. 7 embodiment but which removes contact over the area around the axis where motion is zero or small. The speed of cutting/coagulation will be inversely proportional to the surface area of the flat edge faces.

Figure 9:
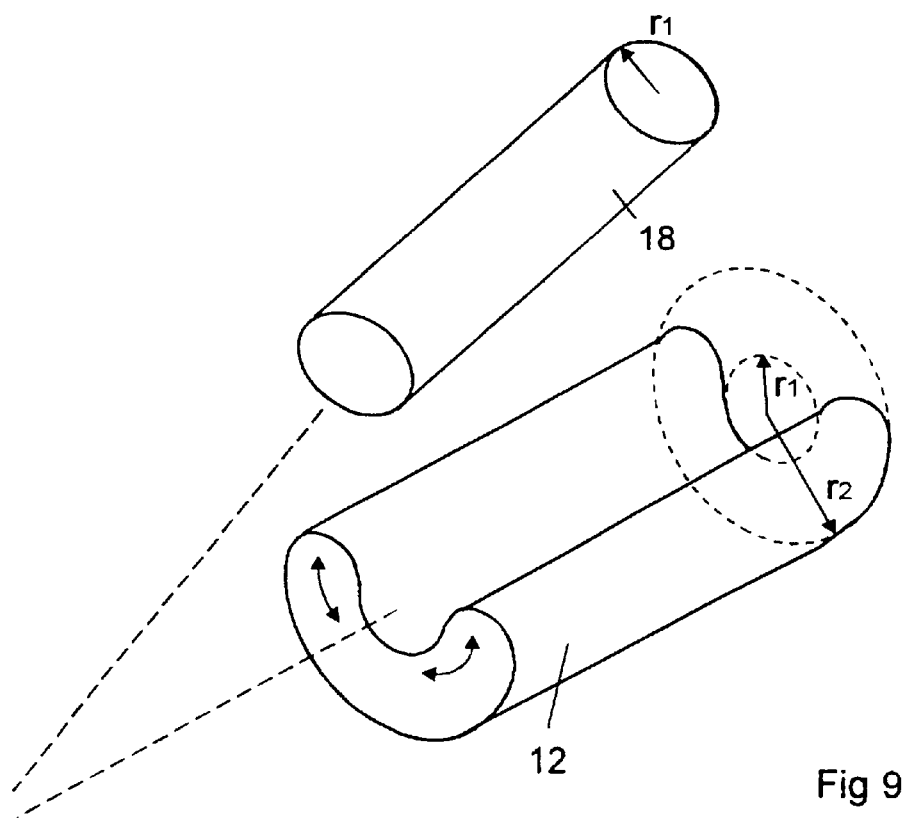
FIG. 9 shows a distal end which embodies a torsional analogue of conventional frictional parallel motion devices.

FIG. 9 shows a torsional analogue of conventional parallel motion devices. A cylindrical static blade 18 of radius $r_1$ traps tissue against a part cylindrical inner surface 19 of radius $r_1$ of a vibrating blade 12 having an external radius of $r_2$. Frictional contact parallel to the torsional motion occurs at an intensity determined by the radius of the cylindrical blade 18. Vibration over this surface is at constant torsional amplitude. Frictional heating is applied to an area determined by radius $r_1$.

Figure 10:
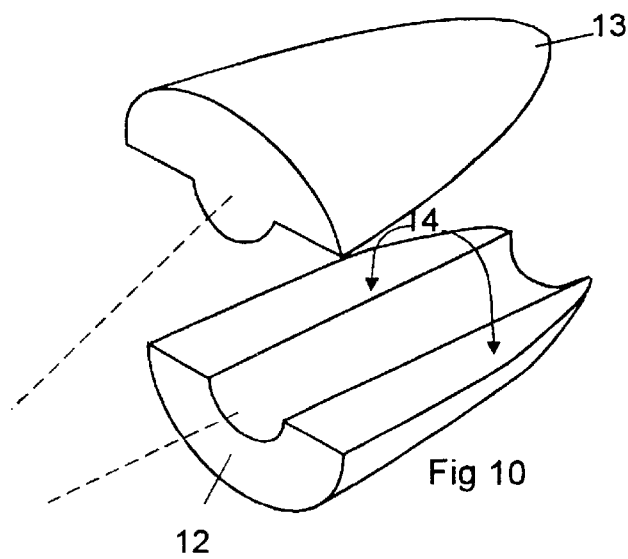
Figure 10:
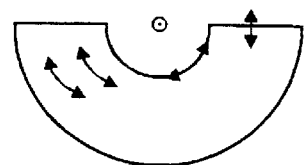

FIG. 10 shows a system combining those shown in FIGS. 8 and 9. Normal motion over edge faces and parallel motion around fixed radius cylindrical ace are produced thus maximising tissue contact with off-axis vibrating faces. The sectional view, FIG. 10A, through the vibrating blade shows both face motions.

Figure 11:
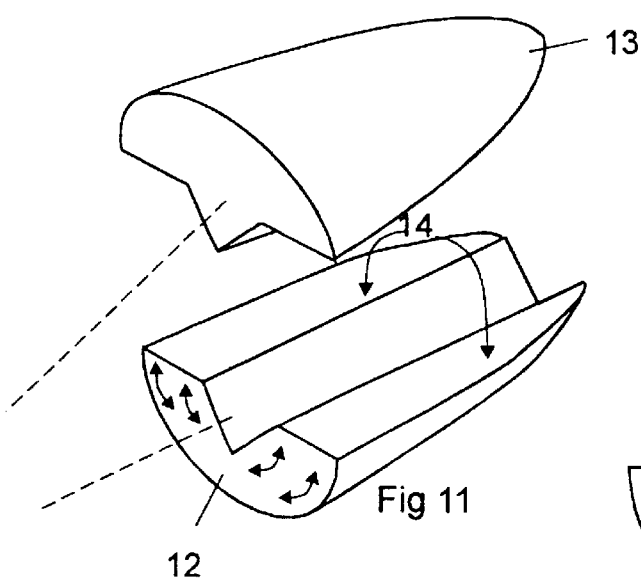
FIGS. 11 and 11A show in perspective and cross sectional view a distal end adapted from that shown in FIG. 10 producing normal motion at edge faces and both normal and parallel components of motion at two planar faces displaced from the axis.
Figure 11A:
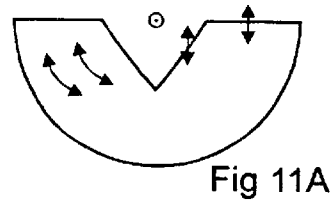

FIG. 11 shows an adaptation of FIG. 10 providing normal motion at edge faces 14 and both normal and parallel components of motion at two planar faces displaced from the axis. As in FIG. 10, tissue is in contact with a moving face off axis but the pure friction effect arising from parallel motion is improved by a component of normal motion. This is shown by the sectional view of FIG. 11A.

Referring to FIG. 12, there is shown a waveguide and amplification horn face in separated condition. End sectional views of each are given. The distal end of the waveguide 4 is of greater diameter than the waveguide itself. A shroud or isolating sleeve 17 surrounds all but the distal cutting end 41 of the waveguide 4. This maximises the usefulness of the working (distal) end but implies connection of the waveguide 4 to the torsional head 1 after insertion, basal end first, through the sleeve 17. The basal end of the waveguide is therefore smaller than the internal diameter of the isolating sleeve 17 and the diameter of the working (distal) end may be equal to the outside diameter of the shroud 17. In order to connect, for torsional vibration, the basal end of the waveguide 4 to the torsional vibratable head 1, a positively connecting cross sectional configuration is required. Alternative connection shapes are shown in FIG. 13.

Figure 14:
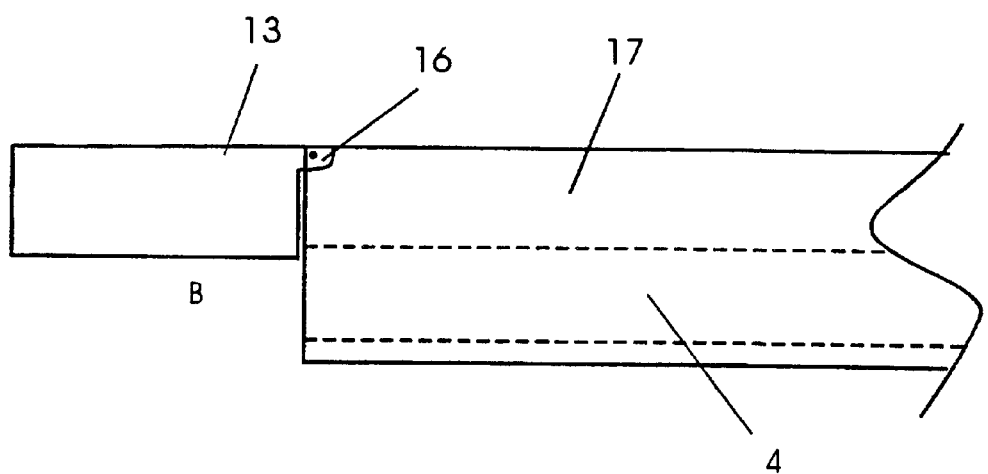
FIG. 14 shows schematically and as a scrap view a distal end of the apparatus.

FIG. 14 shows generally an arrangement at a distal end of a tool. A static anvil 13 (i.e. non-vibrating member) is hingedly connected at 16 to a sleeve 17 which surrounds the waveguide 4 (which waveguide may be connected to an appropriate tool at B, said tool cooperating with the anvil 13).

Figure 15:
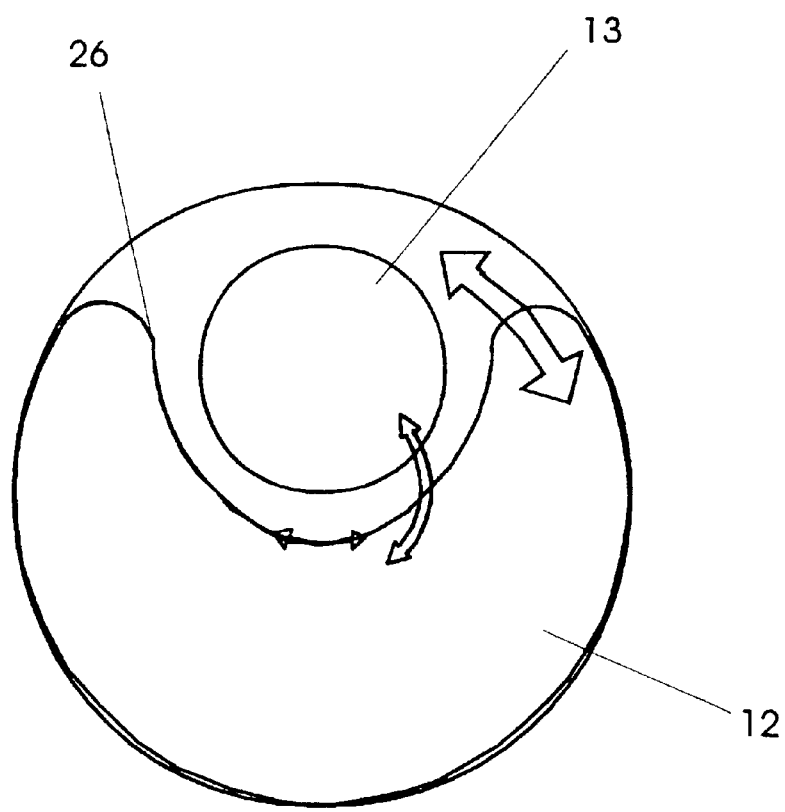
FIG. 15 shows schematically and in cross section a distal end adapted particularly for causing coagulation.
Figure 22:
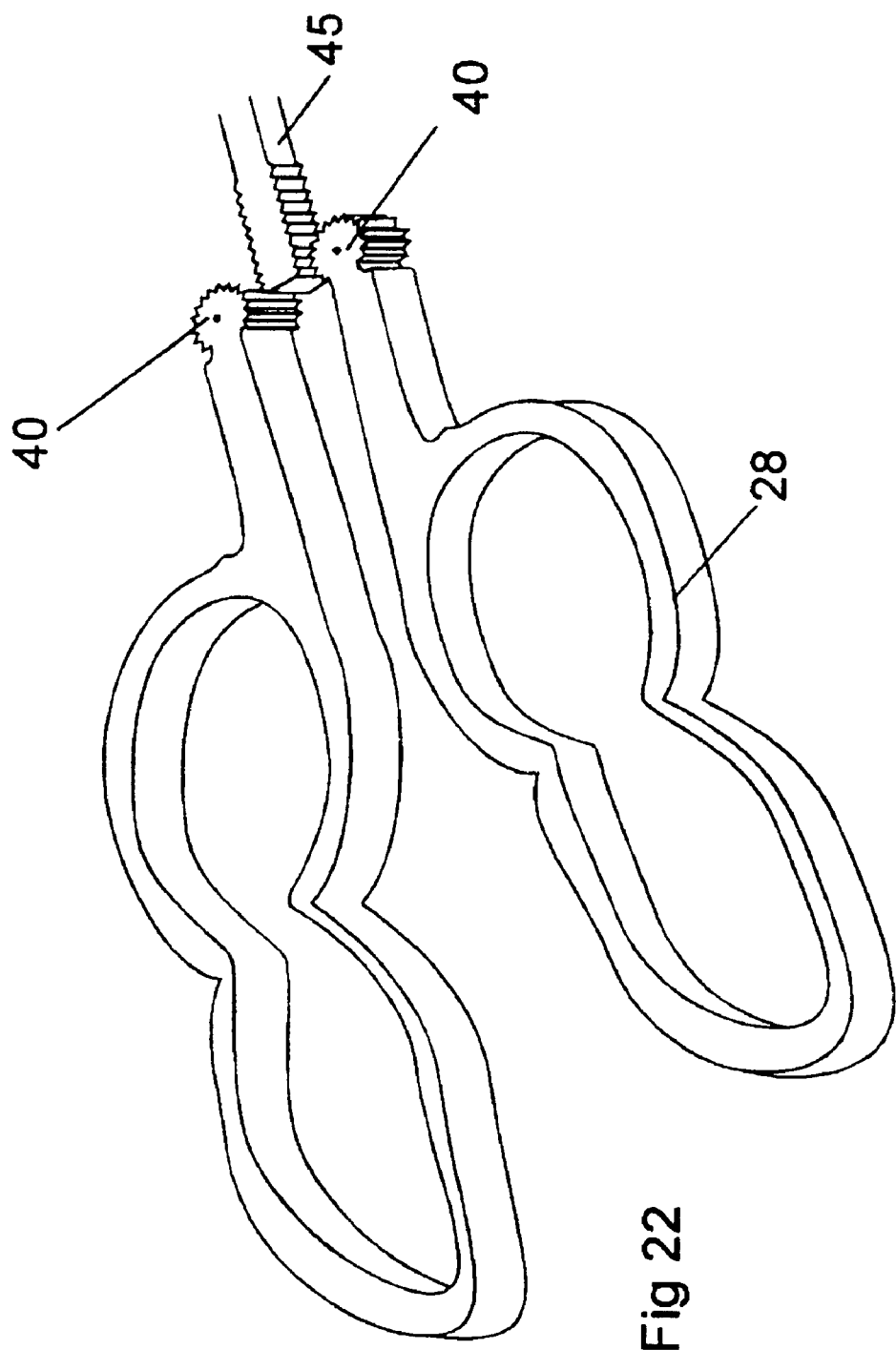
FIG. 22 shows, in perspective and in separated condition, an operating mechanism at a proximal end of the tool including a pair of gripper handles.

FIGS. 15 and 16 show a coagulating or cauterising system in which the vibrating blade 12 has a curved inner surface 26 so shaped that is approximately normal to the motion over a major part of its area. The torsional mode vibration is hence adapted to give optimum cooperation with the static blade 13. This blade 13 is shaped to from a gently curved anvil surface to aid coagulation or cauterisation.

With reference to FIGS. 26 and 27, a variation is shown in which the static blade 13 comprises a shaped surface 44 of PTFE or similar material, attached to a backing and hinge of other material. The shape of the static blade 13 is determined to give a large surface area over which coagulation can occur, with maximum coagulation at the maximum radius of the anvil 13.

FIGS. 17 and 18 show a cutting system. The torsional vibrations are centred about an axis 20 and the magnitude of vibration will depend on the distance of the vibrating point from the axis 20. In a tool as shown in FIGS. 17 and 18, edges 21 and 22, which may be shaped the same or differently, have a large vibrational amplitude and also comprise a relatively large vibrating mass. Hence either one of these edges (they may, if desired, be reversed) is adapted to coact with a shaped surface 24 of anvil 13 for optimum cutting.

A third projecting edge 23, thinner and more flexible than cutting edges 21 and 22 is adapted for free cutting.

Referring to FIG. 19, a combination tool is shown having two, possibly different, cutting edges 29, one of which is adapted at any one time to cooperate with the anvil 13. Other surfaces 25 of the tool may be adapted to provide coagulating or cauterising edges, possibly used in conjunction with an alternatively shaped anvil.

Referring now to FIGS. 20, 20A and 21, a further embodiment of cutting tool is shown. In this case an axial mode driver 2 powered by piezoelectric ceramic transducers 3 is connected to a torsional mode converter 1 operatively connected to the elongate waveguide 4 (preferably a titanium or titanium alloy rod).

The waveguide 4 is housed within an elongate shroud 17 and separated therefrom by spacer discs 27 of PTFE or similar material. An operating rod 26 also passes along the shroud and through the spacer discs 27. At its distal end, the rod 26 is connected to the anvil 13 and at its proximal end the rod 26 may be acted upon, to be movable longitudinally, by operation of a pair of gripper handles 28. The handles 28 are arranged to be movable pivotably one with respect to the other. As they are brought together, in the fashion of scissor handles, the rod 26 is moved forwardly, i.e. towards the distal end, and acts to close the anvil 13 against the end portion of the waveguide 4.

This is shown more clearly in FIGS. 22 to 25. In these, there is shown that each handle 28 is connected to and pivoted about a pinion gear 40. Both pinion gears 40 are adapted to cooperate with a rack 45 which transfers movement of the handles 28 into a longitudinal movement.

As shown in FIG. 26, this longitudinal movement may be transferred by an octagonal or multi-angular inner sleeve 42a. Being multiangular, the sleeve 42a has relatively low frictional contact with the cylindrical sleeve. It is pivoted at point 43 to the anvil 13 so that longitudinal movement of the sleeve 42 will cause the anvil 13 to pivot about point 49.

An alternative arrangement is shown in FIG. 27 where the longitudinal movement is carried by a segment 42b of the sleeve 17.

In both cases, the longitudinal actuator is intended to move with minimal friction within or as part of the sleeve, either by virtue of minimal contact between a multiangular section actuator and a cylindrical sleeve, or by virtue of a minimum profile segment of the sleeve.

Since the amplitude of torsional vibration increases from zero close to the axis to a maximum along the circumference, there is a variation in friction heating which may reduce tissue charring in some areas.

Tissue is trapped between the closing blades and the speed and ease of cutting and blood coagulation will depend on the mode and amplitude of the vibration and the geometry of the blades, designed to utilise the torsional mode of the vibrating blade.

As stated above, in the embodiments of both FIGS. 26 and 27, the static blade 13 comprises a shaped surface 44 of PTFE or similar material, attached to a backing and hinge of other material. The shape of the static blade 13 is determined to give a large surface area over which coagulation can occur, with maximum coagulation at the maximum radius of the anvil 13.

The torsional mode system used to generate the displacement patterns shown in FIGS. 6 to 11, establish that displacement normal to the transmission face occurs in all examples. This ensures maximum transmission into target tissue and contrasts with the parallel displacement associated with the equivalent longitudinal mode system with a passive element, generating friction heating by relative oscillatory motion between the excited blade and tissue.

Theoretical analysis of torsional mode excitation and transmission characteristics indicates that the rotational amplitude gain is proportional to the fourth power of the waveguide diameter ratio, at a stepped interface. There is good correlation with experimental measurements confirming that energy transmission along narrow waveguides can be more efficiently achieved with torsional mode excitation than with an equivalent longitudinal mode system.

What is claimed is:

1. A surgical tool comprising means to generate ultrasonic torsional mode vibrations, a waveguide operatively connected at a proximal end to said generating means and extending a distance therefrom of $n\lambda_{T/2}$, where $\lambda_T$ is the wavelength of ultrasonic vibration in the material of the waveguide, to a distal end provided with blade means which comprise at least one operative facet, the surface of which is transverse to the general direction of said torsional vibrations.

2. A surgical tool according to claim 1, wherein said means to generate ultrasonic torsional mode vibrations comprises a conversion horn and at least one axial mode driver mounted substantially tangentially thereto.

3. A surgical tool according to claim 1, wherein the blade means comprise a torsionally vibratable element connected to said waveguide in combination with a static non-vibratable element.

4. A surgical tool according to claim 3, wherein a shroud is provided to surround and isolate the waveguide along at least a portion of its length.

5. A surgical tool according to claim 4, wherein said non-vibratable static element of the blade means is so mounted to said shroud that it is isolated from said torsional vibrations.

6. A surgical tool according to claim 3, wherein the vibrational element of said blade means has an operative facet directed toward said static element which is substantially normal to the general direction of said torsional vibrations.

7. A surgical tool according to claim 6, wherein the vibrational element is provided with a pair of operative facets, each substantially normal to the direction of said torsional vibrations, said pair of facets intersecting at or adjacent a longitudinal axis of said waveguide.

8. A surgical tool according to claim 3, wherein said static non-vibratable element is mounted to engage selectively said torsionally vibratable element.

9. A surgical tool according to claim 8, wherein said means to cause engagement and disengagement of said elements comprises actuating rod means so connected at its distal end to said static element as to cause pivotal movement thereof into and out of engagement with said vibratable element.

10. A surgical tool according to claim 9, wherein said actuating rod means comprises a tubular member surrounding said waveguide, said tubular member being polygonal in cross-section.

11. A surgical tool according to claim 10, wherein a shroud is provided to surround and isolate the waveguide along at least a portion of its length and said polygonal tubular member is adapted to contact an inner surface of said shroud only at apices of said polygon.

12. A surgical tool according to claim 8, wherein said means to cause engagement and disengagement of said elements comprises actuating rod means connected at its proximal end to manually operable means.

13. A surgical tool according to claim 12, wherein said manually operable means comprise a pair of scissors type grips connected by rack and pinion means to said actuating rod-means.

14. A surgical tool according to claim 13, wherein said actuating rod means comprises a tubular member surrounding said waveguide, said tubular member being polygonal in cross-section.

15. A surgical tool according to claim 14, wherein a shroud is provided to surround and isolate the waveguide along at least a portion of its length and said polygonal tubular member is adapted to contact an inner surface of said shroud only at apices of said polygon.

* * * * *

UNITED STATES PATENT AND TRADEMARK OFFICE
CERTIFICATE OF CORRECTION

PATENT NO. : 6,425,906 B1  
DATED : July 30, 2002  
INVENTOR(S) : Young et al.

It is certified that error appears in the above-identified patent and that said Letters Patent is hereby corrected as shown below:

<u>Title page,</u>
Item [76], Inventors, should read

-- [76]  Inventors:  Michael John Radley Young; Stephen Michael Radley Young, both of Bremridge House, Bremridge, Ashburton, South Devon TQ13 7JX (GB) --

Signed and Sealed this

Second Day of December, 2003

JAMES E. ROGAN
*Director of the United States Patent and Trademark Office*